US012736539B2

(12) United States Patent
Masubuchi et al.

(10) Patent No.: US 12,736,539 B2
(45) Date of Patent: Sep. 15, 2026

(54) QUANTIFICATION METHOD AND LABELING METHOD

(71) Applicants: Konica Minolta, Inc., Tokyo (JP); Kiyoko Harada, Saitama (JP)

(72) Inventors: Manami Masubuchi, Hachioji (JP); Nobuhisa Harada, Koganei (JP); Masaru Takahashi, Kokubunji (JP)

(73) Assignee: Konica Minolta, Inc., Tokyo (JP)

( * ) Notice: Subject to any disclaimer, the term of this patent is extended or adjusted under 35 U.S.C. 154(b) by 441 days.

(21) Appl. No.: 18/569,833

(22) PCT Filed: Mar. 8, 2022

(86) PCT No.: PCT/JP2022/009883
§ 371 (c)(1),
(2) Date: Dec. 13, 2023

(87) PCT Pub. No.: WO2022/264545
PCT Pub. Date: Dec. 22, 2022

(65) Prior Publication Data
US 2024/0295561 A1 Sep. 5, 2024

(30) Foreign Application Priority Data
Jun. 17, 2021 (JP) ................................ 2021-100808

(51) Int. Cl.
*G01N 33/58* (2006.01)
*G01N 21/64* (2006.01)

(52) U.S. Cl.
CPC ....... *G01N 33/582* (2013.01); *G01N 21/6428* (2013.01); *G01N 2021/6441* (2013.01)

(58) Field of Classification Search
CPC ............. G01N 33/582; G01N 21/6428; G01N 2021/6441; G01N 21/64; G01N 21/6458; G01N 33/48; G01N 33/50; G01N 33/53
See application file for complete search history.

(56) References Cited

FOREIGN PATENT DOCUMENTS

| | | |
|---|---|---|
| JP | 2013-46620 A | 3/2013 |
| JP | 2018-84568 A | 5/2018 |

OTHER PUBLICATIONS

English translation of the Written Opinion of the International Searching Authority for corresponding International Appl. No. PCT/JP2022/009883. I (Year: 2022).*

(Continued)

*Primary Examiner* — Brian J. Sines

(74) *Attorney, Agent, or Firm* — RANKIN, HILL & CLARK LLP

(57) ABSTRACT

A quantification method in the present invention is a quantification method for quantifying three or more kinds of quantification-target substances contained in a plurality of samples collected from one specimen, and includes a quantification step of quantifying the three or more kinds of quantification-target substances in each of the plurality of samples on the basis of a detection value derived from a first labeling substance that labels a reference substance commonly contained in the plurality of samples. In the present invention, three or more kinds of observation-target substances can be observed or quantified without requiring many kinds of labeling substances even when staining conditions are different from each other. That is, the observation-target substances (a reference substance and quantification-target substances other than the reference substance) can be each observed or quantified using a smaller number of kinds of labeling substances than the number of kinds of the observation-target substances.

10 Claims, 1 Drawing Sheet

(56) References Cited

OTHER PUBLICATIONS

International Search Report (ISR) dated May 17, 2022 filed in PCT/JP2022/009883.

* cited by examiner

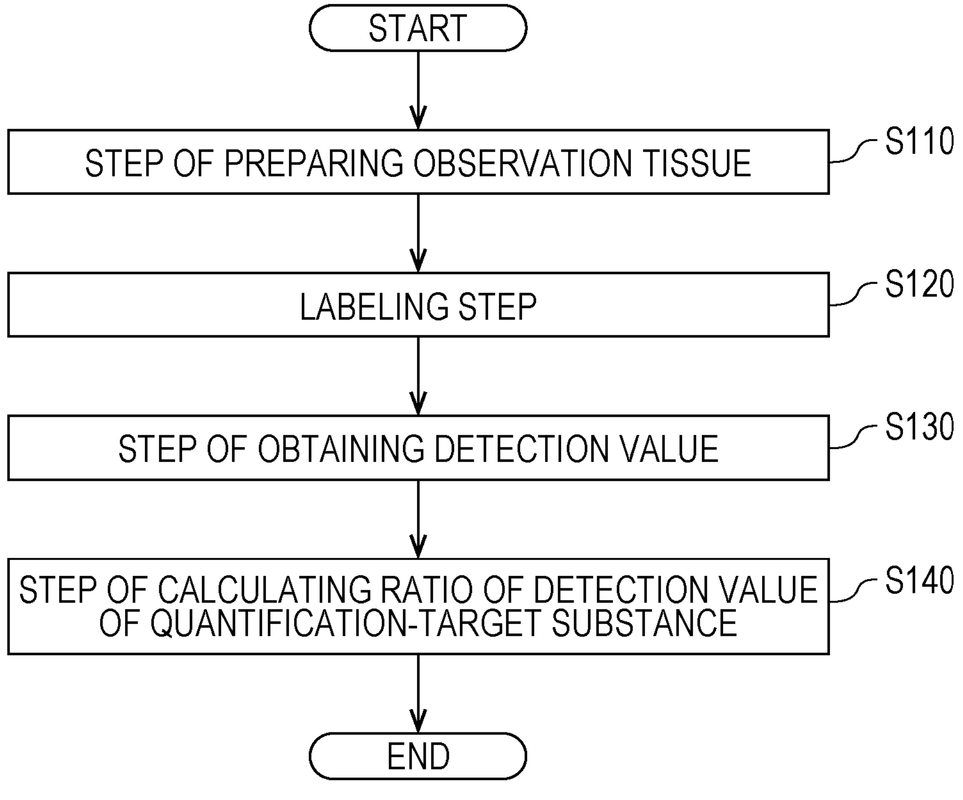
START
STEP OF PREPARING OBSERVATION TISSUE
S110
LABELING STEP
S120
STEP OF OBTAINING DETECTION VALUE
S130
STEP OF CALCULATING RATIO OF DETECTION VALUE OF QUANTIFICATION-TARGET SUBSTANCE
S140
END

QUANTIFICATION METHOD AND LABELING METHOD

TECHNICAL FIELD

The present invention relates to a quantification method for quantifying a plurality of kinds of observation-target substances and a labeling method for labeling an observation-target substance.

BACKGROUND ART

Only a compound evaluated to be effective by screening is selected from candidate compounds to be medicinal drugs. A medicinal drug is often bonded to a target substance such as a receptor, an enzyme, an ion channel, or a transporter in a living body. The medicinal drug reaches a cell, is bonded to a target substance, and then acts on the cell to exhibit drug efficacy. Therefore, determination such as whether a medicinal drug has reached a target substance or whether the reached drug exhibits drug efficacy is an important determination criterion in screening. The above determination is performed using an immunostaining method using a tissue section or the like (See, for example, Patent Literatures 1 and 2.).

Patent Literature 1 describes a method for predicting pathological complete response by immunostaining a tissue section collected from a cancer patient. The method described in Patent Literature 1 predicts pathological complete response by labeling and detecting a cancer marker contained in a tissue section collected from a cancer patient. In addition, as a labeling method, a method using fluorescent nanoparticles is also described. Furthermore, as another labeling method, it is also described that two kinds of cancer markers are stained with two kinds of dyes having different emission wavelengths for one tissue section.

Patent Literature 2 describes a method for identifying a cancer patient by identifying a chromosomal abnormality using fluorescence in situ hybridization (FISH). In the method described in Patent Literature 2, a ratio of each of a plurality of probes to a marker is obtained, and values of the probes in a tissue section are compared to identify a cancer patient.

CITATION LIST

Patent Literature

Patent Literature 1: JP 2018-084568 A
Patent Literature 2: JP 2013-046620 A

SUMMARY OF INVENTION

Technical Problem

Here, in the methods described in Patent Literatures 1 and 2, in order to observe a plurality of kinds of observation-target substances in one tissue section, it is conceivable to increase the number of kinds of labeling substances containing a fluorescent dye. However, when a plurality of kinds of labeling substances (fluorescent dyes) are used, an excitation wavelength and an emission wavelength of each of the fluorescent dyes need to be separated from an excitation wavelength and an emission wavelength of another fluorescent dye. In addition, in a case of observation with a fluorescence microscope, it is also necessary to select a filter corresponding to each of the fluorescent dyes. For these reasons, it is difficult to observe an observation-target substance using three or more kinds of fluorescent dyes, and it is not realistic to observe the observation-target substance using four or more kinds of fluorescent dyes in the first place. Meanwhile, when different kinds of observation-target substances are stained in a plurality of tissue sections, there is no problem of the number of kinds of labeling substances (fluorescent dyes), but it is difficult to completely equalize staining conditions and observation conditions, and it is not easy to accurately compare a fluorescence intensity and the like among the plurality of tissue sections.

In addition, depending on an expression status of an observation-target substance, it may be preferable to change staining conditions for each observation-target substance. When a plurality of kinds of observation-target substances are observed in one tissue section, a plurality of kinds of staining conditions cannot be adopted. Therefore, some observation-target substances (for example, observation-target substances having lower expression) cannot be appropriately stained. Meanwhile, when a plurality of tissue sections are stained, staining conditions can be changed for each of the tissue sections, but if the staining conditions are changed, a fluorescence intensity and the like cannot be accurately compared among the tissue sections.

An object of the present invention is to provide a quantification method and a labeling method capable of more accurately measuring three or more kinds of quantification-target substances without requiring three or more kinds of labeling substances (fluorescent dyes) even when staining conditions are different from each other.

Solution to Problem

A quantification method according to an embodiment of the present invention is a quantification method for quantifying three or more kinds of quantification-target substances contained in a plurality of samples collected from one specimen, and includes a quantification step of quantifying the three or more kinds of quantification-target substances in each of the plurality of samples on the basis of a detection value derived from a first labeling substance that labels a reference substance commonly contained in the plurality of samples.

A labeling method according to an embodiment of the present invention is a method for labeling a plurality of kinds of observation-target substances containing a reference substance contained in each of a plurality of observation tissues collected from one specimen and three or more kinds of quantification-target substances contained in at least one of the plurality of observation tissues, and includes a step of preparing the plurality of observation tissues, and a step of labeling the plurality of kinds of observation-target substances contained in the plurality of observation tissues with different kinds of labeling substances, respectively.

Advantageous Effects of Invention

According to the present invention, it is possible to provide a quantification method and a labeling method capable of measuring relative amounts of three or more kinds of quantification-target substances without requiring four or more kinds of labeling substances (fluorescent dyes) even when staining conditions are different from each other.

BRIEF DESCRIPTION OF DRAWINGS

FIG. 1 is a flowchart of a quantification method according to a first embodiment of the present invention.

DESCRIPTION OF EMBODIMENTS

Hereinafter, a quantification method and a labeling method according to an embodiment of the present invention will be described.

First Embodiment

FIG. 1 is a flowchart of a quantification method according to a first embodiment of the present invention.

The quantification method according to the first embodiment of the present invention is a quantification method for measuring relative amounts of a plurality of kinds of observation-target substances containing a reference substance contained in each of a plurality of observation tissues (samples) collected from one specimen and three or more kinds of quantification-target substances contained in at least one of the plurality of observation tissues. As illustrated in FIG. 1, the quantification method according to the present embodiment may include: a step of preparing a plurality of observation tissues collected from one specimen: a step of labeling a plurality of kinds of observation-target substances contained in the plurality of observation tissues with different kinds of labeling substances, respectively: a step of obtaining detection values derived from the plurality of kinds of labeled observation-target substances; and a step of calculating a ratio of a detection value of a quantification-target substance to a detection value of a reference substance in the plurality of observation tissues.

In the step of preparing an observation tissue, an observation tissue to be used for quantification is prepared (S110). In the present embodiment, in order to compare the amount of an observation-target substance among a plurality of observation tissues, the observation tissues are collected from one specimen. Here, the specimen may be a cell tissue or the like collected from the same individual (for example, a person, an animal, or the like), or may be a cultured cell. In addition, the kind of the observation tissue is not particularly limited as long as an observation-target substance can be detected. Examples of the observation tissue include a pathological tissue, a tissue section such as a cell lone-derived xenograft (CDX) or a patient-derived xenograft (PDX), and a slide specimen from a cultured cell. The number of observation tissues to be prepared is set according to the kind of the quantification-target substance. By preparing a plurality of observation tissues, it is possible to observe a quantitative relationship among a plurality of observation-target substances, localization of the observation-target substances, and the like. In particular, adjacent sections, cell tissues of the same passage, and the like are particularly preferable as the plurality of observation tissues because they more accurately reflect the quantitative relationship among the plurality of observation-target substances, the localization of the observation-target substances, and the like in a specimen.

The observation-target substance contains a reference substance and a quantification-target substance. The reference substance is a substance that can be stably observed and is commonly contained in the plurality of observation tissues. For example, the reference substance is preferably a substance contained in each of the plurality of observation tissues in almost the same amount or a substance whose amount contained in each of the plurality of observation tissues can be grasped in advance. The reference substance functions as a reference marker. The reference substance may be a quantification-target substance or a substance different from the quantification-target substance. The number of kinds of the reference substances may be one or two or more. In the present embodiment, the effect is obtained when the number of kinds of the observation-target substances is three or more.

The quantification-target substance is a substance to be quantified. The quantification-target substance can be relatively quantified by comparison between the quantification-target substance and the reference substance. In addition, for example, as described later, when a table, a calibration curve, or the like for converting a detection value corresponding to each quantification-target substance into an absolute amount thereof is prepared, the quantification-target substance can be absolutely quantified.

The kinds of the reference substance and the quantification-target substance are not particularly limited. Examples of the reference substance and the quantification-target substance include a nucleic acid (DNA, RNA, a polynucleotide, an oligonucleotide, or a peptide nucleic acid (PNA), which may be single-stranded or double-stranded, a nucleoside, a nucleotide, and modified molecules thereof), a protein (a polypeptide, an oligopeptide, a receptor present in a cell membrane of a target cell, or the like), an amino acid (including a modified amino acid), a carbohydrate (an oligosaccharide, a polysaccharide, a sugar chain, or the like), a lipid, exosome, modified molecules thereof, and complexes thereof. More specific examples of the reference substance and the quantification-target substance include 5T4, AXL, BCMA, C4.4A, CA6, Cadherin3, Cadherin6, CEACAM5, CD16, CD19, CD22, CD37, CD56, CD71, CD138, CD142, CD352, DLL3, EphA2, EphrinA4, ETBR, FcγRIII, FOLR1, FGFR2, FGFR3, GCC, HER1 (EGFR), HER2, HER3, HER4, Integrina V, LAMP1, LIV1, Mesothelin, MUC1, MUC16, NaPi2B, Nectin4, NOTCH3, PD-1, PD-L1, PSMA, PTK7, SLAMF7, SLITRK6, STEAP1, TROP2, Ki67, HER4, ER, and PR.

In the labeling step, the reference substance and the quantification-target substance are labeled (S120). A method for labeling the reference substance and the quantification-target substance is not particularly limited. Examples of the method for labeling the reference substance and the quantification-target substance include an immunostaining method using an antibody or a fragment of an antibody, and a staining method using a molecular recognition group similar to an antibody.

In the labeling method by the immunostaining method, an observation tissue (specimen) containing the reference substance and the quantification-target substance is immunostained to obtain an immunostained image in which the reference substance and the quantification-target substance are visualized by fluorescent labeling.

In a secondary reaction of the immunostaining method, a labeling substance containing phosphor integrated particles (fluorescent dye integrated particles) can be used. The phosphor integrated particles (fluorescent dye integrated particles) as a labeling substance are particularly preferable because they have high luminance per particle and make it possible to more accurately observe or quantify the observation-target substance. For example, the reference substance is labeled with a first labeling substance containing fluorescent dye integrated particles, and the quantification-target substance is labeled with a second labeling substance containing fluorescent dye integrated particles having emission wavelengths (colors) different from those of the first labeling substance and having different emission wavelengths from each other. In addition, for example, the reference substance is labeled with two kinds of first labeling substances containing fluorescent dye integrated particles having two different emission wavelengths, and the quantification-target substance is labeled with two kinds of second labeling substances containing fluorescent dye integrated particles having colors different from those of the first labeling substances and having different emission wavelengths from each other. When the fluorescent dye integrated particle contained in the first labeling substance and the fluorescent dye integrated particle contained in the second labeling substance have the same emission wavelength, these fluorescent dye integrated particles cannot be discriminated from each other. For example, the reference substance can be labeled with one kind of first labeling substance, and three or more kinds of quantification-target substances can be labeled with other two kinds of second labeling substances. The number of kinds of the labeling substances including the first labeling substance and the plurality of second labeling substances is preferably smaller than the number of kinds of the observation-target substances including the reference substance and the quantification-target substance. As a result, all the observation-target substances can be observed or quantified with a smaller number of kinds of labeling substances than the number of kinds of the observation-target substances.

The phosphor integrated particle is a nano-sized particle having a structure in which a plurality of phosphors (for example, fluorescent dyes or semiconductor nanoparticles) is contained therein and/or adsorbed on a surface thereof using a particle made of an organic substance or an inorganic substance as a base. Examples of the fluorescent dye constituting the phosphor integrated nanoparticle include a rhodamine-based dye, a Cy-based dye, an Alexa Fluor (registered trademark)-based dye, a BODIPY-based dye, a squarylium-based dye, a cyanine-based dye, an aromatic ring-based dye, an oxazine-based dye, a carbopyronine-based dye, and a pyrromethene-based dye. Examples of a semiconductor nanoparticle material constituting the phosphor integrated nanoparticle include a group II-VI semiconductor, a group III-V semiconductor, and a group IV semiconductor. The phosphor integrated particles can be prepared by a known method (See, for example, JP 2013-57937 A.).

In a method for labeling a reference substance and a quantification-target substance by a staining method using a molecular recognition group similar to an antibody, for example, an aptamer and a SNAP-tag are used as the molecular recognition group.

In the step of obtaining a detection value, a detection value derived from a plurality of kinds of labeled observation-target substances is obtained (S130). A method for obtaining the detection value is appropriately selected on the basis of a labeling substance that labels the observation-target substance. For example, a fluorescence image of an observation tissue labeled with the reference substance and the quantification-target substance, obtained by irradiation with excitation light is captured, and then processed with predetermined image processing software. As a result, for example, when phosphor integrated particles (fluorescent dye integrated particles) are used in the secondary reaction of the immunostaining method, a value (detection value) obtained by summing luminance values derived from the reference substance and a value (detection value) obtained by summing luminance values derived from the quantification-target substance can be obtained. Note that the luminance value may be a value obtained by summing luminance values equal to or more than a predetermined value. The obtained luminance value may be divided by a luminance per phosphor integrated particle (fluorescent dye integrated particle) to be converted into the number of particles. The number of bright spots reflecting emission of the phosphor integrated particles (fluorescent dye integrated particles) that label the observation-target substance may be used as the detection value.

In the step of calculating a ratio of a detection value of a quantification-target substance, each of a plurality of kinds of observation-target substances is quantified on the basis of the detection value (S140). Specifically, a plurality of kinds of quantification-target substances are quantified on the basis of the reference substance. For example, by dividing a luminance value derived from the quantification-target substance by a luminance value derived from the reference substance, a ratio of the quantification-target substance to the reference substance can be obtained. Subsequently, for example, the amount of the quantification-target substance can be quantified on the basis of a calibration curve obtained in advance. Note that, as will be described in the following Examples, when a plurality of reference substances are used, it is confirmed whether the reference substances function appropriately. Specifically, by comparing expression levels of the plurality of reference substances between a plurality of observation tissues, it is confirmed whether the reference substances function appropriately. For example, by comparing fluorescent dye integrated nanoparticle scores based on luminance values of two kinds of reference substances among the observation tissues, it is determined whether or not the two kinds of reference substances are appropriate as reference substances.

(Effect)

As described above, in the present invention, since the reference substance contained in the plurality of observation tissues is labeled with the first labeling substance and the plurality of quantification-target substances (other than the reference substance) contained in the plurality of observation tissues are labeled with the second labeling substance, three or more kinds of observation-target substances can be observed or quantified without requiring many kinds of labeling substances even when staining conditions are different from each other. That is, according to the present invention, the observation-target substances (a reference substance and quantification-target substances other than the reference substance) can be each observed or quantified using a smaller number of kinds of labeling substances than the number of kinds of the observation-target substances. Specifically, a relationship between the number of kinds (N) of the observation-target substances and a minimum number of kinds (n) of the labeling substances can be expressed by the following formula.

$$N = nm - X(m-1)$$

m: number of observation tissues (samples)

X: number of kinds of reference substances

Note that, here, the labeling substances can be regarded as different kinds of labeling substances when they have different main emission wavelengths (colors) as long as detection of the detection value is not hindered. In particular, when the number of kinds of the observation-target substances is four or more, it is very difficult to label the observation-target substances with labeling substances having different main emission wavelengths (colors). However, according to the present invention, more observation-target substances can be observed or quantified with a smaller number of kinds of labeling substances.

Second Embodiment

Next, a labeling method according to a second embodiment of the present invention will be described.

The labeling method according to the second embodiment of the present invention includes: a step of preparing a plurality of observation tissues collected from one specimen and each containing a plurality of kinds of observation-target substances; and a step of labeling the plurality of kinds of observation-target substance contained in each of the plurality of collected observation tissues with a plurality of kinds of labeling substances, respectively. The observation-target substance contains a reference substance contained in each of the plurality of observation tissues and three or more kinds of quantification-target substances contained in at least one of the plurality of observation tissues.

The step of preparing an observation tissue can be performed by the same method as the "step of preparing an observation tissue" in the first embodiment.

The labeling step can be performed by the same method as the "labeling step" in the first embodiment.

(Effect)

As described above, in the labeling method according to the present embodiment, it is possible to prepare a fluorescently labeled observation tissue that can be used in the quantification method according to the first embodiment.

EXAMPLES

Hereinafter, the present invention will be more specifically described with reference to Examples, but the present invention is not limited to the Examples.

1. Preparation of Fluorescent Dye Integrated Nanoparticles (First Labeling Substance and Second Labeling Substance)

As a fluorescent dye, 14.4 mg of Sulforhodamine 101 (Texas Red) as a red fluorescent dye was added to 22 mL of water and dissolved therein. Subsequently, to this solution, 2 mL of a 5% aqueous solution of polyoxyethylene oleyl ether (Emulgen (registered trademark) 430, manufactured by Kao Corporation) as an emulsion polymerization emulsifier was added. Subsequently, the temperature of this solution was raised to 70° C. while the solution was stirred with a hot stirrer. Thereafter, to this solution, 0.65 g of a melamine resin raw material (Nikalac (registered trademark) MX-035, manufactured by Nippon Carbide Industries Co., Ltd.) was added. Subsequently, to this solution, 1000 μL of a 10% aqueous solution of dodecylbenzenesulfonic acid (manufactured by Kanto Chemical Co., Ltd.) as a reaction initiator was added, and the resulting mixture was heated and stirred at 70° C. for 50 minutes. Thereafter, the temperature was raised to 90° C. and heated and stirred for 20 minutes to obtain a dispersion of red fluorescent dye integrated nanoparticles.

The obtained dispersion of nanoparticles was washed with pure water to remove impurities such as an excessive melamine resin raw material and a red fluorescent dye. Specifically, the dispersion was centrifuged at 20000 G for 15 minutes in a centrifuge (micro cooled centrifuge Model 3740, manufactured by Kubota Corporation). The supernatant was removed. Thereafter, ultrapure water was added to the residue, and the resulting mixture was irradiated with an ultrasonic wave to be redispersed. An operation of centrifugation, removal of a supernatant, and redispersion in ultrapure water was repeated five times. Red fluorescent dye integrated nanoparticles (excitation wavelength: 590 nm, emission wavelength: 620 nm) were prepared through the above steps.

By using a Pyrromethene 556 dye in place of Sulforhodamine 101 (Texas Red) dye in the preparation of the red fluorescent dye integrated nanoparticles, green fluorescent dye integrated nanoparticles (excitation wavelength: 490 nm, emission wavelength: 520 nm) were prepared.

By using a Cy5 dye in place of Sulforhodamine 101 (Texas Red) dye in the preparation of the red fluorescent dye integrated nanoparticles, near infrared fluorescent dye integrated nanoparticles (excitation wavelength: 643 nm, emission wavelength: 647 nm) were prepared.

2. Modification of Fluorescent Dye Integrated Nanoparticles

Maleimide was introduced into an end of the red fluorescent dye integrated nanoparticle using an N-Hydroxy succinimide-polyethylene glycol (NHS-PEG)-maleimide reagent, and then a thiolated antibody was bonded thereto. This was taken as "immunostain A (first labeling substance) ".

Maleimide was introduced into an end of the green fluorescent dye integrated nanoparticle, and then a thiolated antibody was bonded thereto. This was taken as "immunostain B (second labeling substance)".

Maleimide was introduced into an end of the near infrared fluorescent dye integrated nanoparticle, and then a thiolated antibody was bonded thereto. This was taken as "immunostain C (second labeling substance)".

Example 1

In the present Example, an example is illustrated in which three sections were treated with the same protocol, and seven observation-target substances (HER2, EGFR, HER3, Ki67, HER4, ER, and PR) including one reference substance (HER2) and six quantification-target substances (EGFR, HER3, Ki67, HER4, ER, and PR) were quantified.

Tissues of a breast cancer patient were collected, formalin-fixed paraffin-embedded tissue blocks were prepared by a conventional method, and sections 1 to 3 continuously sliced with a microtome were prepared.

(Sample Pretreatment Step)

Each of the sections was deparaffinized. Thereafter, washing for water replacement was performed. Each of the washed sections was boiled in a 0.1 M citrate buffer (pH 6.0) at 95° C. for 40 minutes to activate an antigen. Each of the activated sections was washed, and each of the washed sections was blocked using PBS containing 1% BSA for 15 minutes.

In the section 1, HER2, EGFR, and HER3 were used as the observation-target substances.

In the section 2, HER2, Ki67, and HER4 were used as the observation-target substances.

In the section 3, HER2, ER, and PR were used as the observation-target substances.

As described above, HER2 is a reference substance. EGFR, HER3, Ki67, HER4, ER and PR are quantification-target substances.

A combination of each of the sections, an immunostain, an antibody, and fluorescent dye integrated nanoparticles is presented in Table 1.

TABLE 1

| | Immunostain A | Immunostain B | Immunostain C |
|---|---|---|---|
| Section 1 | Anti-HER2 antibody-bonded red fluorescent dye integrated nanoparticles | Anti-EGFR antibody-bonded green fluorescent dye integrated nanoparticles | Anti-HER3 antibody-bonded near infrared fluorescent dye integrated nanoparticles |
| Section 2 | Anti-HER2 antibody-bonded red fluorescent dye integrated nanoparticles | Anti-Ki67 antibody-bonded green fluorescent dye integrated nanoparticles | Anti-HER4 antibody-bonded near infrared fluorescent dye integrated nanoparticles |
| Section 3 | Anti-HER2 antibody-bonded red fluorescent dye integrated nanoparticles | Anti-ER antibody-bonded green fluorescent dye integrated nanoparticles | Anti-PR antibody-bonded near infrared fluorescent dye integrated nanoparticles |

Fluorescent dye integrated nanoparticle staining and a method for acquiring a fluorescent dye integrated nanoparticle score are as follows.

(Immunostaining Step)

Using PBS containing 1% (w/w) of BSA, a reaction solution containing each of immunostain A, immunostain B, and immunostain C at a concentration of 0.1 nM was prepared. Each of the sections that had been subjected to the specimen pretreatment step was immersed in the reaction solution, and was caused to react at room temperature for two hours.

(Fixing Step)

Each of the immunostained sections was washed with PBS, and then each of the sections was fixed with a 4% neutral paraformaldehyde solution for ten minutes.

(Morphological Observation Staining Step)

Each of the fixed sections was stained with a Mayer's hematoxylin solution for one minute to be subjected to hematoxylin staining, and then washed with running water for five minutes.

(Sample Post-Treatment Step)

An operation of immersing each of the sections (stained sections) after the morphological observation staining step in pure ethanol for five minutes was performed four times to perform dehydration. Subsequently, an operation of immersing each of the sections in xylene for five minutes was performed three times. Finally, mounting was performed in which a mounting medium (Marinol, MUTO CHEMICAL CO., LTD.) was placed on each of the stained sections and covered with a cover glass to obtain a stained section used for observation.

(Fluorescence Microscope Observation and Imaging Step)

In order to acquire an immunostained image (400 fold) of each of the stained sections after the specimen post-treatment step, a fluorescence microscope (BX-63; Olympus Corporation) and a digital camera for a microscope (DP80; Olympus Corporation) attached to the fluorescence microscope were used. Wavelengths of excitation light and fluorescence for observing and imaging the fluorescent dye integrated nanoparticle of each color are as presented in Table 2, and were set using an excitation light optical filter and a fluorescence optical filter included in a fluorescence microscope, respectively. Exposure time at the time of imaging was adjusted such that a luminance of an image was not saturated, and set to, for example, 30 ms.

The wavelength of excitation light and the wavelength of fluorescence for each of the immunostains are presented in Table 2.

TABLE 2

| | Immunostain A | Immunostain B | Immunostain C |
|---|---|---|---|
| Wavelength of excitation light | 576 to 596 nm | 455 to 485 nm | 625 to 655 nm |
| Wavelength of fluorescence | 612 to 644 nm | 500 to 550 nm | 665 to 715 nm |

As for imaging, imaging a morphological observation hematoxylin stained image of cells in a bright visual field of a fluorescence microscope and imaging an immunostained image of each color in the same visual field were performed for five visual fields per stained section.

(Image Processing and Measurement Step)

For image processing, "ImageJ" (open source) as image processing software was used. The shape of a cell (the position of a cell nucleus) was specified by image processing using a morphological observation stained image, and superimposed on the immunostained image to extract a bright spot representing a fluorescent dye integrated nanoparticle of each color labeled with each observation-target substance. Subsequently, a bright spot having a luminance of a predetermined value or more was extracted, and a total luminance of the bright spots was divided by a luminance per the fluorescent nanoparticle to calculate the number of particles per visual field. Then, the number of bright spots of each observation-target substance was measured in five visual fields per stained section, converted into the number of fluorescent nanoparticles per unit area (100 $\mu m^2$), and an average value thereof was calculated and taken as a "fluorescent dye integrated nanoparticle score" of the section.

The calculated fluorescent dye integrated nanoparticle score is presented in Table 3.

TABLE 3

| | Immunostain A | Immunostain B | Immunostain C |
|---|---|---|---|
| Section 1 | 461 | 381 | 285 |
| Section 2 | 487 | 84 | 192 |
| Section 3 | 443 | 38 | 102 |

A ratio of a fluorescent dye integrated nanoparticle score of each marker to a fluorescent dye integrated nanoparticle score of HER2 stained with immunostain A is presented in Table 4.

TABLE 4

| | Immunostain A | Immunostain B | Immunostain C |
|---|---|---|---|
| Section 1 | 1 (461/461) | 0.83 (381/461) | 0.62 (285/461) |

TABLE 4-continued

| | Immunostain A | Immunostain B | Immunostain C |
|---|---|---|---|
| Section 2 | 1 (487/487) | 0.17 (84/487) | 0.39 (192/487) |
| Section 3 | 1 (443/443) | 0.09 (38/443) | 0.23 (102/443) |

As presented in Table 4, it was found that expression occurred at a ratio of HER2:EGFR:HER3:Ki67:HER4:ER: PR=1:0.83:0.62:0.17:0.39:0.09:0.23. As described above, relative amounts of the seven kinds of substances could be measured using particles of three colors (fluorescent dyes).

Finally, the amount of the observation-target substance was obtained on the basis of a calibration curve prepared in advance.

Example 2

In the present Example, an example is illustrated in which three sections were treated with different protocols, and four observation-target substances (HER2, EGFR, Ki67, and ER) including one reference substance (HER2) and three quantification-target substances (EGFR, Ki67, and ER) were quantified.

Tissues of a breast cancer patient were collected, formalin-fixed paraffin-embedded tissue blocks were prepared by a conventional method, and sections 1 to 3 continuously sliced with a microtome were prepared.

The section 1 was boiled in a 0.1 M citrate buffer (pH 6) at 95° C. for 40 minutes to be activated. In the section 1, HER2 and EGFR were used as the observation-target substances.

The section 2 was autoclaved in a 0.1 M citrate buffer (pH 6) at 121° C. for five minutes to be activated. In the section 2, HER2 and Ki67 were used as the observation-target substances.

The section 3 was autoclaved in a 1 M Tris-HCl buffer (pH 9) at 121° C. for five minutes to be activated. In the section 3, HER2 and ER were used as the observation-target substances.

A combination of each of the sections, an immunostain, an antibody, and fluorescent dye integrated nanoparticles is presented in Table 5.

TABLE 5

| | Immunostain A | Immunostain B |
|---|---|---|
| Section 1 | Anti-HER2 antibody-bonded red fluorescent dye integrated nanoparticles | Anti-EGFR antibody-bonded green fluorescent dye integrated nanoparticles |
| Section 2 | Anti-HER2 antibody-bonded red fluorescent dye integrated nanoparticles | Anti-Ki67 antibody-bonded green fluorescent dye integrated nanoparticles |
| Section 3 | Anti-HER2 antibody-bonded red fluorescent dye integrated nanoparticles | Anti-ER antibody-bonded green fluorescent dye integrated nanoparticles |

Fluorescent dye integrated nanoparticle staining and a method for acquiring a fluorescent dye integrated nanoparticle score are the same as those in Example 1.

A calculated fluorescent dye integrated nanoparticle score is presented in Table 6.

TABLE 6

| | Immunostain A | Immunostain B |
|---|---|---|
| Section 1 | 490 | 415 |
| Section 2 | 639 | 120 |
| Section 3 | 1214 | 108 |

A ratio of a fluorescent dye integrated nanoparticle score of each marker to a fluorescent dye integrated nanoparticle score of HER2 stained with immunostain A is presented in Table 7.

TABLE 7

| | Immunostain A | Immunostain B |
|---|---|---|
| Section 1 | 1 (490/490) | 0.84 (415/490) |
| Section 2 | 1 (639/639) | 0.19 (120/639) |
| Section 3 | 1 (1214/1214) | 0.09 (108/1214) |

As presented in Table 7, it was found that expression occurred at a ratio of HER2:EGFR:Ki67:ER=1:0.84:0.19: 0.09. As described above, even when different activation treatments were performed for the sections, relative amounts of the four kinds of substances could be measured using particles of two colors (fluorescent dyes).

Finally, the amount of the observation-target substance was obtained on the basis of a calibration curve prepared in advance.

Example 3-1

In the present Example, an example is illustrated in which three sections were treated with different protocols, and five observation-target substances (HER2, EGFR, HER3, HER4, and PR) including two reference substances (HER2 and EGFR) and three quantification-target substances (HER3, HER4, and PR) were quantified.

Tissues of a breast cancer patient were collected, formalin-fixed paraffin-embedded tissue blocks were prepared by a conventional method, and sections 1 to 3 continuously sliced with a microtome were prepared. Each of the sections was deparaffinized. Thereafter, washing for water replacement was performed.

The section 1 was boiled in a 0.1 M citrate buffer (pH 6) at 95° C. for 40 minutes to be activated. In the section 1, HER2, EGFR, and HER3 were used as the observation-target substances.

The section 2 was autoclaved in a 0.1 M citrate buffer (pH 6) at 121° C. for five minutes to be activated. In the section 2, HER2, EGFR, and HER4 were used as the observation-target substances.

The section 3 was autoclaved in a 1 M Tris-HCl buffer (pH 9) at 121° C. for five minutes to be activated. In the section 3, HER2, EGFR, and PR were used as the observation-target substances.

A combination of each of the sections, an immunostain, an antibody, and fluorescent dye integrated nanoparticles is presented in Table 8.

TABLE 8

| | Immunostain A | Immunostain B | Immunostain C |
|---|---|---|---|
| Section 1 | Anti-HER2 antibody-bonded red fluorescent dye integrated nanoparticles | Anti-EGFR antibody-bonded green fluorescent dye integrated nanoparticles | Anti-HER3 antibody-bonded near infrared fluorescent dye integrated nanoparticles |
| Section 2 | Anti-HER2 antibody-bonded red fluorescent dye integrated nanoparticles | Anti- EGFR antibody-bonded green fluorescent dye integrated nanoparticles | Anti-HER4 antibody-bonded near infrared fluorescent dye integrated nanoparticles |
| Section 3 | Anti-HER2 antibody-bonded red fluorescent dye integrated nanoparticles | Anti- EGFR antibody-bonded green fluorescent dye integrated nanoparticles | Anti-PR antibody-bonded near infrared fluorescent dye integrated nanoparticles |

Fluorescent dye integrated nanoparticle staining and a method for acquiring a fluorescent dye integrated nanoparticle score are the same as those in Example 1.

A calculated fluorescent dye integrated nanoparticle score is presented in Table 9.

TABLE 9

| | Immunostain A | Immunostain B | Immunostain C |
|---|---|---|---|
| Section 1 | 442 | 382 | 263 |
| Section 2 | 681 | 591 | 283 |
| Section 3 | 1347 | 1081 | 318 |

A ratio of each marker to HER2 stained with immunostain A (upper row) and a ratio of each marker to EGFR stained with immunostain B (lower row) are presented in Table 10.

TABLE 10

| | Immunostain A | Immunostain B | Immunostain C |
|---|---|---|---|
| Section 1 | 1 (442/442) | 0.87 (382/442) | 0.60 (263/442) |
| | 1.2 (442/382) | 1 (382/382)) | 0.69 (263/382) |
| Section 2 | 1 (681/681) | 0.87 (591/681) | 0.42 (283/681) |
| | 1.2 (681/591) | 1 (591/591) | 0.48 (283/591) |
| Section 3 | 1 (1347/1347) | 0.80 (1081/1347) | 0.23 (318/1347) |
| | 1.2 (1347/1081) | 1 (1081/1081) | 0.29 (318/1081) |

As presented in Table 10, there was no significant difference in a ratio to HER3, a ratio to HER4, and a ratio to PR between a case where HER2 stained with immunostain A was used as a reference substance and a case where EGFR stained with immunostain B was used as a reference substance. From this, when HER2 is used as a reference substance or when EGFR is used as a reference substance, the ratio to HER3, the ratio to HER4, and the ratio to PR can be appropriately determined. As described above, even when different activation treatments were performed for the sections, relative amounts of the five kinds of substances could be measured using particles of three colors (fluorescent dyes).

Finally, the amount of the observation-target substance was obtained on the basis of a calibration curve prepared in advance.

Example 3-2

In the present Example, an example is illustrated in which three sections were treated with different protocols, and five observation-target substances (HER2, EGFR, HER3, HER4, and PR) including two reference substances (HER2 and EGFR) and three quantification-target substances (HER3, HER4, and PR) were compared.

Tissues of a breast cancer patient were collected, formalin-fixed paraffin-embedded tissue blocks were prepared by a conventional method, and sections 1 to 3 continuously sliced with a microtome were prepared. Each of the sections was deparaffinized. Thereafter, washing for water replacement was performed.

The section 1 was boiled in a 0.1 M citrate buffer (pH 6) at 95° C. for 40 minutes to be activated. In the section 1, HER2, EGFR, and HER3 were used as the observation-target substances.

The section 2 was autoclaved in a 1 M Tris-HCl buffer (pH 9) at 121° C. for five minutes to be activated. In the section 2, HER2, EGFR, and HER4 were used as the observation-target substances.

The section 3 was autoclaved in a 1 M Tris-HCl buffer (pH 9) at 121° C. for 15 minutes to be activated. In the section 3, HER2, EGFR, and PR were used as the observation-target substances.

A combination of each of the sections, an immunostain, an antibody, and fluorescent dye integrated nanoparticles is presented in Table 11.

TABLE 11

| | Immunostain A | Immunostain B | Immunostain C |
|---|---|---|---|
| Section 1 | Anti-HER2 antibody-bonded red fluorescent dye integrated nanoparticles | Anti-EGFR antibody-bonded green fluorescent dye integrated nanoparticles | Anti-HER3 antibody-bonded near infrared fluorescent dye integrated nanoparticles |
| Section 2 | Anti-HER2 antibody-bonded red fluorescent dye integrated nanoparticles | Anti- EGFR antibody-bonded green fluorescent dye integrated nanoparticles | Anti-HER4 antibody-bonded near infrared fluorescent dye integrated nanoparticles |

TABLE 11-continued

| | Immunostain A | Immunostain B | Immunostain C |
|---|---|---|---|
| Section 3 | Anti-HER2 antibody-bonded red fluorescent dye integrated nanoparticles | Anti- EGFR antibody-bonded green fluorescent dye integrated nanoparticles | Anti-PR antibody-bonded near infrared fluorescent dye integrated nanoparticles |

Fluorescent dye integrated nanoparticle staining and a method for acquiring a fluorescent dye integrated nanoparticle score are the same as those in Example 1.

A calculated fluorescent dye integrated nanoparticle score is presented in Table 12.

TABLE 12

| | Immunostain A | Immunostain B | Immunostain C |
|---|---|---|---|
| Section 1 | 442 | 382 | 263 |
| Section 2 | 1350 | 1153 | 564 |
| Section 3 | 1298 | 1320 | 342 |

A ratio of a fluorescent dye integrated nanoparticle score of each marker to a fluorescent dye integrated nanoparticle score of HER2 stained with immunostain A (upper row) and a ratio of a fluorescent dye integrated nanoparticle score of each marker to a fluorescent dye integrated nanoparticle score of EGFR stained with immunostain B (lower row) are presented in Table 13.

TABLE 13

| | Immunostain A | Immunostain B | Immunostain C |
|---|---|---|---|
| Section 1 | 1<br>(442/442) | 0.86<br>(382/442) | 0.60<br>(263/442) |
| | 1.2<br>(442/382) | 1<br>(382/382) | 0.69<br>(263/382) |
| Section 2 | 1<br>(1350/1350) | 0.85<br>(1153/1350) | 0.42<br>(564/1350) |
| | 1.2<br>(681/1153) | 1<br>(591/1153) | 0.49<br>(564/1153) |
| Section 3 | 1<br>(1298/1298) | 1.02<br>(1320/1298) | 0.26<br>(342/1298) |
| | 0.98<br>(1298/1320) | 1<br>(1320/1320) | 0.26<br>(342/1320) |

As described above, when HER2 and EGFR are used as reference substances, the fluorescent dye integrated nanoparticle scores of HER2 and EGFR are correlated with each other (See Example 3-1). However, in the present Example, as presented in Table 13, when HER2 was used as a reference marker, an expression level of EGFR to HER2 was 0.86 in the section 1 and 0.85 in the section 2, but was 1.02 in the section 3. Meanwhile, when EGFR was used as a reference marker, an expression level of HER2 to EGFR was 1.2 in the section 1 and 1.2 in the section 2, but 0.98 in the section 3. That is, in the sections 1 and 2, the fluorescent dye integrated nanoparticle score of HER2 and the fluorescent dye integrated nanoparticle score of EGFR are appropriate as reference substances, but in the section 3, the fluorescent dye integrated nanoparticle score of HER2 and the fluorescent dye integrated nanoparticle score of EGFR are not appropriate as reference substances.

In the section 3, since the fluorescent dye integrated nanoparticle score of HER2 and the fluorescent dye integrated nanoparticle score of EGFR are almost the same value, it is considered that the fluorescent dye integrated nanoparticle score of EGFR has reached an upper limit value. Thus, when the reference substance is not appropriate, a value of the reference substance is not used.

That is, in the present Example, it is found that expression occurred at a ratio of HER2:EGFR:HER3:HER4:PR=1.2:1:0.69:0.49:0.26. As described above, when two or more kinds of reference substances are used, inappropriate values can be excluded, and thus the quantification-target substance can be quantified more accurately. Even when different activation treatments were performed for the sections, relative amounts of the five kinds of substances could be measured using particles of three colors (fluorescent dyes).

Finally, the amount of the quantification-target substance was obtained on the basis of a calibration curve prepared in advance. As a result, the absolute amount of the quantification-target substance can be obtained. In the above Examples, observation and quantification were performed using one or more kinds of quantification-target substances as reference substances. However, even when a substance different from the quantification-target substances is used as a reference substance, the same effect can be obtained, and each observation-target substance can be observed or quantified with a smaller number of kinds of labeling substances than the number of kinds of the observation-target substances (a reference substance and a quantification-target substance).

The present application claims priority based on Japanese Patent Application No. 2021-100808 filed on Jun. 17, 2021. Contents described in the application specification and drawings are all incorporated herein by reference.

INDUSTRIAL APPLICABILITY

The present invention is useful, for example, for screening a medicinal drug, proving a mechanism of an action of a medicinal drug, and evaluating toxicity of a medicinal drug.

The invention claimed is:

1. A quantification method for quantifying three or more kinds of quantification-target substances contained in a plurality of samples collected from one specimen, the quantification method comprising quantifying the three or more kinds of quantification-target substances in each of the plurality of samples on a basis of a detection value derived from a first labeling substance that labels a reference substance commonly contained in the plurality of samples.

2. The quantification method according to claim 1, wherein the reference substance is one or more kinds of quantification-target substances among the three or more kinds of quantification-target substances.

3. The quantification method according to claim 1, wherein in the quantifying, the three or more kinds of quantification-target substances are quantified on a basis of detection values derived from a plurality of second labeling substances that label quantification-target substances other than the reference substance, respectively.

4. The quantification method according to claim 1, wherein the reference substance is a substance different from the three or more kinds of quantification-target substances.

5. The quantification method according to claim 1, wherein in the quantifying, the three or more kinds of quantification-target substances are quantified on a basis of detection values derived from a plurality of second labeling substances that label the three or more kinds of quantification-target substances, respectively.

6. The quantification method according to claim 3, wherein the first labeling substance contains fluorescent dye integrated particles, and the second labeling substance contains fluorescent dye integrated particles having emission wavelengths different from those of the first labeling substance and having different emission wavelengths from each other.

7. The quantification method according to claim 6, wherein the number of kinds of the labeling substances including the first labeling substance and the plurality of second labeling substances is smaller than the number of kinds of the observation-target substances including the reference substance and the quantification-target substance.

8. The quantification method according to claim 5, wherein the first labeling substance contains fluorescent dye integrated particles, and the second labeling substance contains fluorescent dye integrated particles having emission wavelengths different from those of the first labeling substance and having different emission wavelengths from each other.

9. A labeling method for labeling a plurality of kinds of observation-target substances containing a reference substance contained in each of a plurality of observation tissues collected from one specimen and three or more kinds of quantification-target substances contained in at least one of the plurality of observation tissues, the labeling method comprising:

preparing the plurality of observation tissues; and labeling the plurality of kinds of observation-target substances contained in the plurality of observation tissues with different kinds of labeling substances, respectively.

10. The labeling method according to claim 9, wherein the reference substance is labeled with a first labeling substance containing fluorescent dye integrated particles, and the three or more kinds of quantification-target substance are labeled with a second labeling substance containing fluorescent dye integrated particles having colors different from those of the first labeling substance and having different colors from each other.

* * * * *